United States Patent [19]
Gabbay

[11] Patent Number: 5,935,163
[45] Date of Patent: Aug. 10, 1999

[54] NATURAL TISSUE HEART VALVE PROSTHESIS

[75] Inventor: Shlomo Gabbay, Short Hills, N.J.

[73] Assignee: Shelhigh, Inc., Millburn, N.J.

[21] Appl. No.: 09/052,707

[22] Filed: Mar. 31, 1998

[51] Int. Cl.[6] .................................................. A61F 2/24
[52] U.S. Cl. ............................................................ 623/2
[58] Field of Search ........................................ 623/2, 900

[56] References Cited

U.S. PATENT DOCUMENTS

| | | |
|---|---|---|
| 3,744,060 | 7/1973 | Bellhouse et al. ............................. 623/2 |
| 3,983,581 | 10/1976 | Angell et al. . |
| 4,247,292 | 1/1981 | Angell et al. . |
| 4,388,735 | 6/1983 | Ionescu et al. . |
| 4,477,930 | 10/1984 | Totten et al. . |
| 4,626,255 | 12/1986 | Reichart et al. . |
| 4,759,758 | 7/1988 | Gabbay . |
| 5,156,621 | 10/1992 | Navia et al. . |
| 5,336,258 | 8/1994 | Quintero et al. . |
| 5,549,665 | 8/1996 | Vesely et al. . |

FOREIGN PATENT DOCUMENTS 2 136 533  9/1994  United Kingdom ....................... 623/2

*Primary Examiner*—David H. Willse
*Attorney, Agent, or Firm*—Tarolli, Sundheim, Covell Tummino & Szabo

[57] ABSTRACT

A heart valve prosthesis (88; 128) having a plurality of leaflets (18, 20 and 22; 138, 140 and 142). The valve (10; 130) is covered with a sheath (90; 172) of natural tissue. The sheath (90; 172) extends from an inflow end (12; 132) of the valve (10; 130) beyond an outflow end (14; 134) of the valve (12; 132) to define a plurality of lobes (98, 100 and 102; 182, 184 and 186). A substantially flexible annular ring (60; 162) may be positioned between the sheath (90; 172) and the heart valve (10; 132) to provide additional stability.

27 Claims, 3 Drawing Sheets

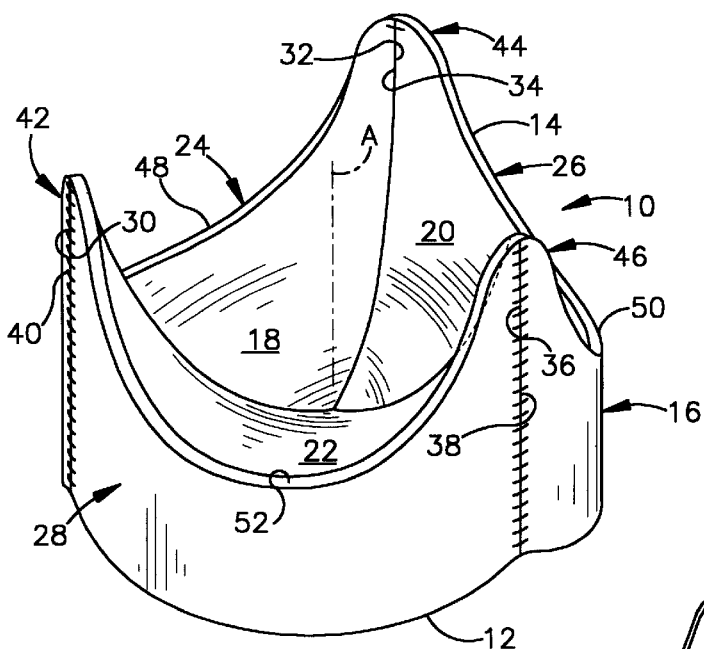

ced side wall portions define commissures. The heart valve prosthesis also includes an outer sheath of natural tissue covering the outer surface of the heart valve. The outer sheath has an outflow end that extends beyond the outflow end of the heart valve adjacent the commissures to define a plurality of lobes.

NATURAL TISSUE HEART VALVE PROSTHESIS

TECHNICAL FIELD

The present invention relates to a BIOS-prosthesis, and more particularly to a natural tissue heart valve prosthesis and a method for making the prosthesis.

BACKGROUND OF THE INVENTION

Numerous types of heart valve prostheses have been developed for replacing defective heart valves in human patients. One common type of heart valve prosthesis includes a natural tissue heart valve mounted within a sent. The sent generally provides strength and rigidity to the heart valve. Typically, the sent is covered with a textile material, such as Dacron™, which provides a substrate to which the heart valve may be secured. While the sent provides desired rigidity and strength, which inhibits the inward deflection of the sent posts, it also decreases the hemodynamics of the valve. This is because the stent substantially increases the side wall thickness of the prosthesis, which reduces the size of the flow orifice for a prosthesis having a given outer diameter. The textile covering also tends to abrade cusps of the valve.

In order to overcome the disadvantages associated with the stented heart valve prosthesis, there has been an increasing tendency to form natural tissue heart valve prostheses with no stent. These are called stentless valves. Stentless valves exhibit improved hemodynamics and are less resistant to blood flow. In addition, stentless valves, as compared to stented valves, are more resistant to structural failure because the rigidity of a stent can cause damage to the moving cusps. The improved hemodynamic characteristics of stentless valves also can cause beneficial remodeling of the heart muscle. Specifically, it has been determined that several months after implantation of a stentless valve in the aortic position, there is a noticeable improvement in the size of a left ventricle.

Even though a stentless prosthesis offers improved results over its stented counterpart, in practice, conventional stentless prostheses have not been completely satisfactory. It requires a greater degree of surgical proficiency to implant a stentless prosthesis. It usually also requires additional time to perform the procedure. Accordingly, a very small number of surgeons are willing to implant a stentless valve.

There also are technical problems associated with the implantation of a typical natural tissue heart valve prosthesis having no stent. In general, a stentless prosthesis is deformable. Thus, if the aortic annulus is calcified, the implanted valve can be deformed and become dysfunctional. Such deformation of the valve might cause the cusps to be unleveled, resulting in inadequate coaptation of the cusps and backflow. It also has been determined that the sizing of stentless valves is not well defined for surgeons. Therefore, a sizing mismatch may occur, which can cause the valve to be stenotic or insufficient.

SUMMARY OF THE INVENTION

The present invention is directed to a heart valve prosthesis that includes a natural tissue heart valve having a generally cylindrical side wall portion extending between an inflow end and an outflow end of the heart valve. The side wall portion has an outer surface. The heart valve also includes a plurality of leaflets disposed within the side wall portion of the valve. Each of the leaflets has an associated side wall portion and side edges. Adjacent side edges of adjacent leaflets and adjacent portions of their respective associated side wall portions define commissures. The heart valve prosthesis also includes an outer sheath of natural tissue covering the outer surface of the heart valve. The outer sheath has an outflow end that extends beyond the outflow end of the heart valve adjacent the commissures to define a plurality of lobes.

Another feature of the present invention is directed to a method of making a heart valve prosthesis. The method includes the step of providing a heart valve having an inflow end, an outflow end, and a generally cylindrical side wall portion extending between the inflow end and the outflow end. The heart valve also includes a plurality of leaflets disposed within the side wall portion. Each of the leaflets has an associated side wall portion and a pair of side edges, with adjacent side edges of adjacent leaflets and adjacent portions of their respective associated side wall portions defining commissures. The method also includes attaching an annular ring of a substantially flexible material about the side wall portion of the valve positioned intermediate the inflow and outflow ends of the valve. A sheath of pericardial tissue covers the annular ring and the outer surface of the heart valve. The sheath has an inflow end portion and an outflow end portion. The outflow end portion of the sheath is extended beyond the outflow end of the heart valve to define a plurality of lobes adjacent the commissures.

BRIEF DESCRIPTION OF THE DRAWINGS

Preferred embodiments of the present invention are illustrated in the accompanying drawings, in which:

FIG. 1 is a perspective view of a heart valve used in an embodiment of the present invention;

FIG. 2 is a perspective view of a ring used in an embodiment of the present invention;

FIG. 3 is another embodiment of a ring which may be used as a substitute for the ring of FIG. 2;

DESCRIPTION OF PREFERRED EMBODIMENTS

Figure 4:
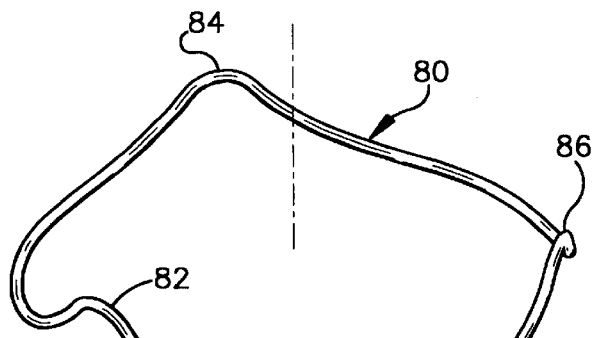
FIG. 4 is yet another embodiment of a ring.

FIG. 1 illustrates a preferred embodiment of a natural tissue heart valve, generally indicated at 10. The heart valve 10 includes an inflow end 12, an outflow end 14 and a central axis, indicated at A, extending through the inflow and outflow ends 12 and 14, respectively. The valve 10 also has a generally cylindrical side wall portion 16 formed of a valve wall extending between the inflow end 12 and the outflow end 14. The heart valve 10 also includes a plurality of leaflets or cusps 18, 20 and 22 mounted within the side wall portion 16. Each of the leaflets 18, 20 and 22 has a respective associated side wall portion 24, 26 and 28 and respective pairs of opposed side edges 30 and 32, 34 and 36 and 38 and 40. Adjacent pairs of side edges 30 and 40, 32 and 34, 36 and 38 together with adjacent portions of their respective associated side wall portions 24, 26 and 28 define commissures, indicated at 42, 44 and 46. The heart valve 10 also sinuses 48, 50 and 52 formed in the outflow end 14 of the valve 10 between adjacent commissures 42 and 44, 44 and 46, and 46 and 42, respectively.

The heart valve illustrated in FIG. 1 is a tri-composite natural tissue heart valve. In particular, each of the leaflets 18, 20 and 22 are selected to be of similar size, shape and symmetry. Matching the leaflets 18, 20 and 22 in this manner generally provides an improved operation of the tri-composite valve over complete heart valves, which have asymmetric valve leaflets.

Preferably, each of the leaflets 18, 20 and 22 is a non-coronary leaflet, suitably from an aortic porcine valve. Non-coronary leaflets generally experience enhanced durability because of. the fibrous attachment of each leaflet 18, 20 and 22 to its respective valve wall portion 24, 26 and 28. The leaflets 18, 20 and 22 and associated valve wall portions 24, 26 and 28 may be excised from an appropriate valve, which has been tanned or fixed. For example, a valve may be fixed in a 0.3 to 0.5 glutaraldehyde solution at a temperature ranging between about 15° C. and 25° C. A pressure between 0 and 4 millimeters mercury (HG) may also be applied to the outflow end of a valve to maintain the leaflets in a desired closed position.

The side edges 30 and 32, 34 and 36, and 38 and 40 of the associated valve wall portion 24, 26 and 28 of each respective leaflet 18, 20 and 22 of the composite heart valve 10 are attached, suitably by sutures, to the side edges of each adjacent associated leaflet, as shown in FIG. 1. The tri-composite heart valve 10 should be assembled such that there is substantial coaptation, or generally axial engagement along the axis A, between each of the leaflets 18, 20 and 22 when in the closed position. This arrangement provides for substantially simultaneous opening and closing of the leaflets 18, 20 and 22 to permit blood flow through the valve 10 as well as to inhibit blood backflow.

It will be apparent to those skilled in the art that the composite heart valve 10 is similar in appearance and operation to a complete heart valve. A complete heart valve, such as an aortic porcine valve or other suitable heart valve, may also be used in connection with the present invention.

Figure 5:
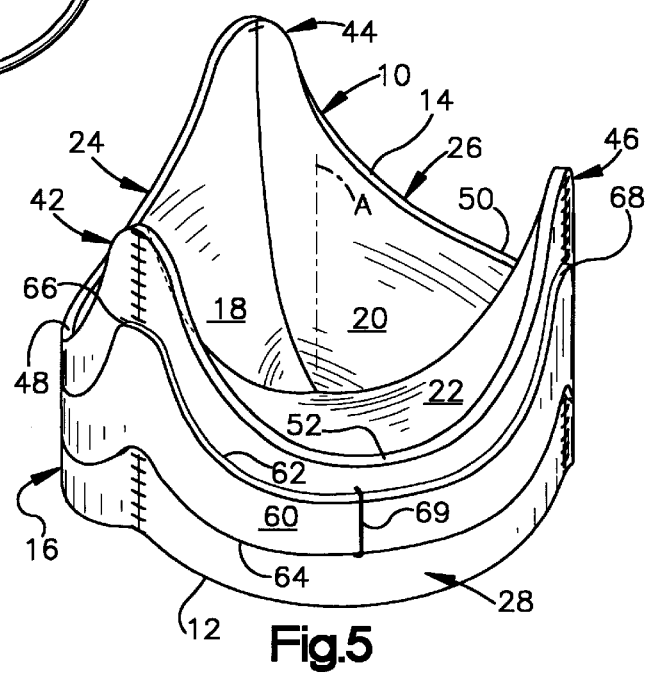
FIG. 5 is a perspective view illustrating the ring of FIG. 3 attached to the heart valve of FIG. 1.

Referring to FIG. 5, an annular ring 60 is positioned around the valve wall 16 intermediate the inflow and outflow ends 12 and 14, respectively. Three alternative embodiments of suitable rings 60, 70 and 80 are illustrated in FIGS. 2, 3 and 4, respectively. Each of the rings 60, 70 and 80 is formed of a substantially flexible and resilient material, preferably having maximum memory to return to its original shape after being stressed. In general, the ring 60, 70 and 80 stabilizes the heart valve prosthesis during implantation.

The ring 60, 70 or 80 also has a known outer diameter, suitably ranging in a variety of predetermined sizes. This provides an practical and accurate way to determine the size of the resulting prosthesis. Based upon the size of the ring 60, 70 or 80, a surgeon may select an appropriately sized prosthesis for implantation without a significant likelihood of a sizing mismatch between the prosthesis and the patient.

The ring 60 illustrated in FIG. 2 is formed of a synthetic resin material, which may be a plastic material, such as Delrin™. Preferably, the ring 60 has a radial thickness of less than about 0.5 millimeters. The ring 60 also has an inner diameter that approximates the outer diameter of the heart valve 10 to which it is attached, such that the ring 60 engages the side wall portion 16. The ring 60 has an outflow edge 62 dimensioned and configured according to the contour of the outflow end 14 of the valve 10. Specifically, the outflow edge 62 of the ring 60 is sinusoidal having peaks 66, 67 and 68 that are spaced apart circumferentially to correspond to the circumferential positioning and shape of the commissures 42, 44 and 46. Preferably, the axial length of the ring 60 at the peaks 66, 67 and 68 is from about ⅓ to about ⅔ the axial length of the valve 10 along the respective commissures 42, 44 and 46. The ring 60 also has inflow edge 64 contoured according to the inflow end 12 of the valve 10.

The ring 60 is positioned coaxially around the valve 10, such as by sliding it over the side wall portion 16. The ring 60 is positioned intermediate the inflow and outflow ends 12 and 14, respectively, as shown in FIG. 5. The respective inflow and outflow edges 64 and 62 of the ring preferably are spaced apart from the respective inflow and outflow ends 12 and 14 of the valve 10. The peaks 66, 67 and 68 are aligned with the respective commissures 42, 44 and 46. Once in position, one or more sutures 69 may be applied to secure the ring 60 to the side wall portion 16 of the valve 10.

With respect to the embodiment of FIG. 3, the ring 70 includes an outflow edge 72 and an inflow edge 74, which are dimensioned and configured to correspond to the contour of the respective outflow end 14 and inflow end 12 of the heart valve 10 to which it is to be attached. The outflow edge 72 of the ring 70 is preferably sinusoidal, with peaks 76, 77 and 78 dimensioned and configured according to the commissures 42, 44 and 46 of the valve 10. In this embodiment, the ring 70 is formed of two spaced apart layers 71 and 73 of thin, flexible and resilient wire. A plurality of axially extending connecting rods 75 are connected between the layers 71 and 73 to maintain the spaced apart relationship of the layers 71 and 73.

The annular ring 80 shown in FIG. 4 is formed of a single layer of a thin, flexible and resilient wire. The single layer ring 80 is dimensioned and configured to correspond to the dimensions and configuration of the outflow end 14 of the valve 10 to which it is to be attached. Specifically, the ring 80 includes peaks 82, 84 and 86 dimensioned and spaced according to the commissures 42, 44 and 46 of the valve 10.

The double layer ring 70 and the single layer ring 80 are attached to a heart valve 10 in a manner substantially identical to that shown and described with respect to FIG. 5. Each ring 70 or 80 will be positioned around the outer surface of the valve wall 16 with the peaks 76, 77 and 78 or 82, 84 and 86 of the ring 70 or 80 aligned with a respective commissure 42, 44 and 46. The rings 70 or 80 should be positioned intermediate the respective outflow and inflow ends 14 and 12 of the valve 10, such as is shown in FIG. 5 for the ring 60. Once appropriately positioned, the rings 70 or 80 may be secured to the side wall portion 16 of the valve 10, suitably by one or more sutures.

It will be apparent to those skilled in the art that while three embodiments of rings 60, 70 and 80 are shown and described herein, other configurations of ring structures may also be used. It also will be apparent that the peaks of each respective ring 60, 70 or 80 will be substantially symmetrical for a tri-composite valve, such as shown in FIG. 1, and asymmetrical for a complete valve (not shown).

Figure 6:
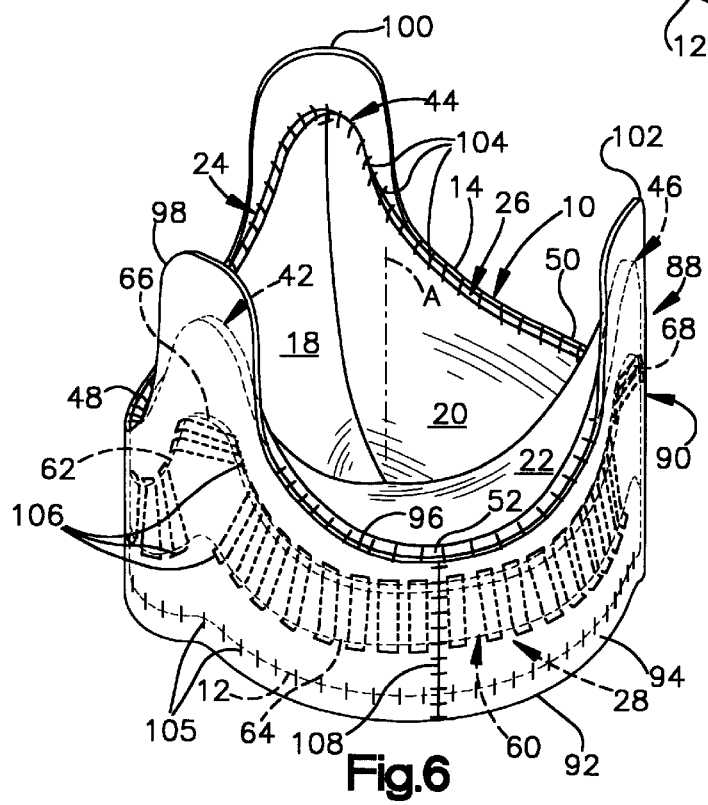
FIG. 6 is a perspective view of an embodiment of a heart valve prosthesis in accordance with the present invention.

A preferred embodiment of a heart valve prosthesis 88 in accordance with the present invention is illustrated in FIG. 6. A thin sheath 90 of natural tissue is applied over and covers the ring 60 and the side wall portion 16 of the valve 10. The sheath 90 preferably is formed of pericardium, suitably porcine or equine pericardium which has been appropriately fixed in a glutaraldehyde solution. The sheath 90 has an inflow end portion 92 that extends beyond the inflow end 12 of the heart valve 10 to define an implantation flange, indicated at 94. The sheath 90 also includes an outflow end portion 96 having a plurality of ear-shaped flanges or lobes 98, 100 and 102 extending beyond the outflow end 14 of the valve 10. The lobes 98, 100 and 102 extend a predetermined distance beyond and lateral to each of the commissures 42, 44 and 46 at the outflow end 14 of the valve 10. The lobes 98, 100 and 102 preferably extend from about three to about four millimeters above the respective commissures and 42, 44 and 46. The lobes 98, 100 and 102 might also extend a greater distance beyond each respective commissure 42, 44 and 46. The surgeon implanting the prosthesis 88 may thus cut the lobes 98, 100 and 102 to a desired shape and size. The particular size of the lobes 98, 100 and 102 also will depend upon the size of the prosthesis 88. Intermediate each of the lobes 98, 100 and 102, the outflow end 96 of the sheath 90 also follows the contour of the valve sinuses 48, 50 and 52. The sheath 90 is secured to outflow end 14 of the valve 10, such as by a plurality of sutures 104. Similarly, the inflow end 12 of the valve 10 may be secured to the sheath 90 by sutures 105. When implanting prosthesis 88, the lobes 98, 100 and 102 may conveniently be sewn to the aortic valve wall of the patient. Consequently, the aortic valve wall of the patient will inhibit the inward deflection of the commissures 42, 44 and 46, thereby maintaining a desired shape of the prosthesis 88. Preferably,the ring 60, 70 or 80 configured to be substantially flexible, such that the ring cannot of its own strength inhibit the deflection of the commissures 42, 44 and 46 during closure of the leaflets 18, 20 and 22.

The sheath 90 also includes a pair of side edges that are secured edge to edge, suitably by sutures, to form an axial seam 108. The seam 108 preferably is positioned in the middle of one leaflet 28 intermediate adjacent commissures 42 and 46.

The sheath 90 also is secured about the ring 60, such as by sutures 106 sewn through the sheath 90 and through the side wall portion of the 16 of the side wall portion valve along the inflow and outflow edges 62 and 64 of the ring 60. Preferably, "mattress sutures" 106 between the sheath 90 and the ring 60 are used to maintain the axial positioning of the ring 60 intermediate the inflow and outflow ends 12 and 14 of the heart valve 10, as shown in FIG. 6.

Figure 7:
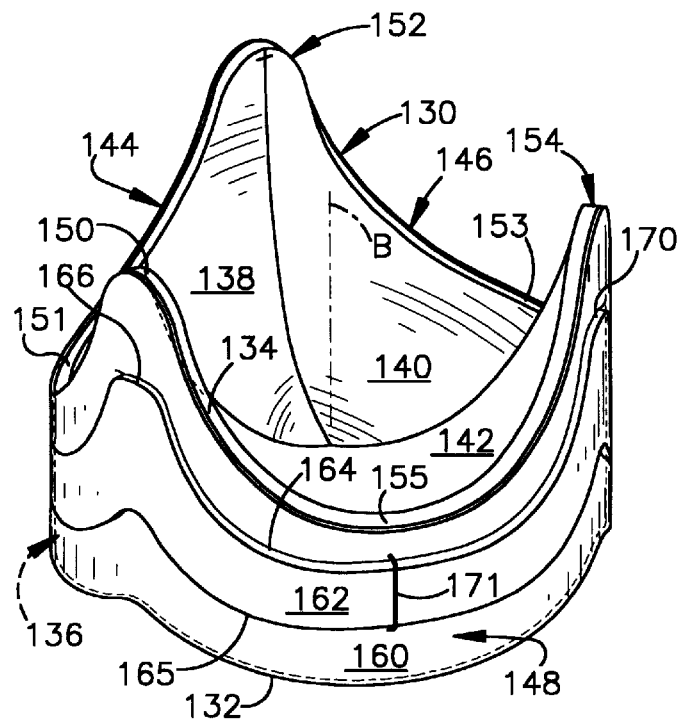
FIG. 7 is a perspective view illustrating the ring of FIG. 3 attached to a valve structure, which may be used in another embodiment of the present invention.
Figure 8:
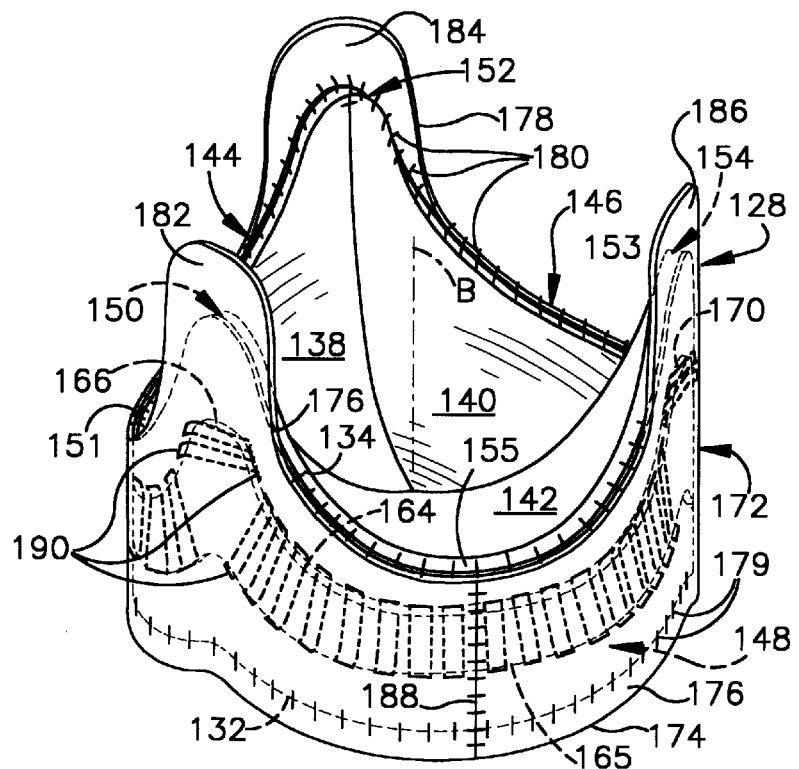
FIG. 8 is a perspective view of another embodiment of a heart valve prosthesis in accordance with the present invention.

An alternative embodiment of a heart valve prosthesis 128 is shown in FIG. 8. FIG. 7 illustrates an intermediate step in the fabrication process of the prosthesis 128 of FIG. 8. The prosthesis 128 includes a natural tissue heart valve 130, which may be substantially similar to the valve 10 shown and described with respect to FIG. 1.

The heart valve 130 may be a complete heart valve or a composite heart valve, although a composite valve is preferred. The heart valve 130 includes an inflow end 132, an outflow end 134 and a generally cylindrical side wall portion 136 extending between the inflow end 132 and the outflow end 134. The side wall portion 136 is defined by the valve wall portion of the heart valve 10. The heart valve has an axis, indicated at B, extending through the inflow and outflow ends 132 and 134, respectively. The composite heart valve 130 also includes a plurality of similarly sized, similarly shaped and symmetrical leaflets 138, 140 and 142. Each leaflet 138, 140 and 142 has an associated side wall portion 144, 146 and 148, respectively, which define the side wall portion 136. In the composite valve 130, adjacent leaflets 138, 140 and 142 are attached at their adjacent side edges of the side wall portions 144, 146 and 148, suitably by suture, to define commissures, indicated at 150, 152 and 154. The heart valve 130 also includes sinuses 151, 153, and 155 formed in the outflow end 134 of the valve 130 between adjacent respective commissures 150 and 152, 152 and 154, and 154 and 150.

The prosthesis 128 includes a first sheath 160 of natural tissue, such as a thin sheet of equine or porcine pericardium, covering the outer surface of the valve 130 intermediate the inflow and outflow end portions 132 and 134, respectively. The first sheath 160 is secured to the side wall portion 136, suitably by sutures (not shown), along at least a portion of the inflow and outflow ends 132 and 134 of the valve 130. Preferably, the first sheath 160 covers substantially the entire side wall portion 136 of the valve 130, as shown in FIG. 7.

An annular ring 162, which, for example, can be one of the rings 60, 70 and 80 shown and described with respect to FIGS. 2, 3 and 4, is positioned coaxially around the first sheath 160 and the valve 130 and intermediate the inflow and outflow ends 132 and 134 of the valve 130. The ring 162 includes an outflow end 164 dimensioned and configured according to the contour of the outflow end 134 of the valve 130. More particularly, the ring 162 has a sinusoidal outflow end 164 having peaks 166 and 170 spaced circumferentially to correspond to the respective commissures 150 and 154. The ring 162 also includes an inflow end 165 contoured according to the inflow end 132 of the valve 130. The ring 162 is positioned around the valve 130, such that the axial length of the ring 162 at the peaks 166 and 170 extends from about ⅓ to about ⅔ the axial length of the heart valve 130 at the respective commissures 150 and 154. The ring 162 May be secured to the first sheath 160 by one or more sutures, indicated at 171. This will maintain a desired axial position of the ring 162 until additional sutures may be applied as described below.

After the ring 162 has been applied to the valve 130 and the first sheath 160, a cylindrical outer sheath 172 of a natural tissue, such as a thin sheet of pericardium, is applied around valve structure of FIG. 7. Specifically, the outer sheath 172 covers the ring 162, the first sheath 160, and the exposed side wall portion 136 of the heart valve 130, as illustrated in FIG. 8. The outer sheath 172 has an inflow end portion 174 that extends beyond the inflow end 132 of the heart valve 130 to define an implantation flange, indicated at 176. The outer sheath 172 also includes an outflow end portion 178 having a plurality of lobes 182, 184 and 186 extending beyond the outflow end 134 of the valve 130. The lobes 182, 184 and 186, which may be ear-shaped flanges, preferably extend a predetermined distance beyond and lateral to each of the commissures 150, 152 and 154 at the outflow end 134 of the valve 130. The outflow end portion 178 of the outer sheath 172 also follows the contour of the sinuses 151, 153 and 155 intermediate each of the commissures 150, 152 and 154. The outer sheath 172 is secured to the valve 130 and the inner sheath 160 along the inflow and outflow ends 132 and 134 of the valve 130, suitably by respective sutures 179 and 180. The lobes 182, 184 and 186 may conveniently be sewn to the aortic valve wall of the patient, thereby, inhibiting the inward deflection of the commissures 150, 152 and 154 during operation of the prosthesis 128.

The outer sheath 172 includes an axial seam 188, which is formed by suturing its ends together. The seam 188 preferably is positioned in the middle of one leaflet 142 between adjacent commissures 150 and 154. The outer sheath 172 also is secured to the side wall portion 136 of the valve 130 and about the ring 162, such as by "mattress sutures" 190. The sutures 190 maintain the axial positioning of the ring 162 spaced apart from and intermediate the respective inflow and outflow ends 132 and 134 of the heart valve 130.

From the foregoing description it will be apparent to those skilled in the art that the present invention provides an improved heart valve prosthesis 88 or 128, which may be termed "semi-stentless." The prosthesis 88 or 128 exhibits hemodynamics comparable to known stentless valves. The flexible ring 60, 70, 80 or 162 provides a "skeleton" to stabilize the prosthesis 88 or 128, without significantly increasing its side wall thickness. The ring 60, 70, 80 or 162 also will resist deformation of the prosthesis 88 or 128 and promote desired coaptation of the leaflets 18, 20 and 22 or 138, 140 and 142. In addition, the prosthesis 88 or 128 exposes only natural tissue and sutures, thereby providing biocompatibility with the patient.

From the above description of the invention, those skilled in the art will perceive improvements, changes and modifications. Such improvements, changes and modifications within the skill of the art are intended to be covered by the appended claims.

Having described the invention, the following is claimed:

1. A heart valve prosthesis comprising:

a natural tissue heart valve having an inflow end, an outflow end, and a generally cylindrical side wall portion extending between said inflow end and said outflow end, said valve including a plurality of leaflets, each of said leaflets having an associated side wall portion and side edges, adjacent side edges of adjacent said leaflets and adjacent portions of respective said associated side wall portions defining commissures;

an annular ring of a substantially flexible material positioned around said valve wall intermediate said inflow and outflow ends; and a sheath of natural tissue attached around said valve wall and said ring, said sheath having an inflow end extending beyond said inflow end of said heart valve and defining an implantation flange, said sheath having an outflow end with a plurality of lobes extending beyond said outflow end of said heart valve.

2. The heart valve prosthesis of claim 1 further comprising a sinus formed in said outflow end of said valve between adjacent said commissures.

3. The heart valve prosthesis of claim 2 wherein said outflow end of said sheath follows the contour of each of said sinuses.

4. The heart valve prosthesis of claim 1 wherein said sheath is made of pericardium.

5. The heart valve prosthesis of claim 1 wherein each of said lobes extends a predetermined distance beyond and lateral to each of said commissures at said outflow end of said heart valve.

6. The heart valve prosthesis of claim 5 wherein each of said lobes comprises an ear-shaped flange.

7. The heart valve prosthesis of claim 1 wherein said heart valve comprises a composite heart valve formed of three heart valve leaflets of generally similar size, shape and symmetry, each said leaflet including a valve wall portion having an inflow end, an outflow end and a pair of generally opposed side edges extending between the inflow and outflow ends, said side edges of each of said leaflets being attached to said side edges of adjacent leaflets such that there is substantial coaptation between said leaflets, adjacent side edges of adjacent leaflets defining said commissures, and said valve wall portions of said composite heart valve leaflets defining said side wall portion of said heart valve.

8. The heart valve prosthesis of claim 7 wherein each of said leaflets is a non-coronary leaflet of an aortic heart valve.

9. The heart valve prosthesis of claim 1 wherein said ring comprises a plastic material having a substantially thin side wall portion.

10. The heart valve prosthesis of claim 9 wherein said side wall portion of said ring has a thickness less than about 0.5 mm.

11. The heart valve prosthesis of claim 9 wherein said side wall portion of said ring has a substantially short axial length relative to the axial length of said side wall portion of said heart valve.

12. The heart valve prosthesis of claim 1 wherein said ring comprises a resilient thin wire member.

13. The heart valve prosthesis of claim 1 wherein said ring is sinusoidal with peaks corresponding to the contour of said outflow end of said heart valve, said ring being attached around said heart valve such that the axial length of said ring at said peaks is less than about two-thirds the axial length of said valve along corresponding said commissures.

14. A heart valve prosthesis comprising:

a natural tissue heart valve comprising:

a generally cylindrical side wall portion extending between an inflow end and an outflow end, said side wall portion having an outer surface; and a plurality of leaflets dispose&ed within said side wall portion, each of said leaflets having side edges and an associated side wall portion, adjacent side edges of adjacent said leaflets and respective adjacent portions of said associated side wall portions defining commissures;

an outer sheath of natural tissue covers said outer surface of said heart valve, said outer sheath having an outflow end portion extending beyond said outflow end of said heart valve adjacent said commissures to define a plurality of lobes.

15. The heart valve prosthesis of claim 14 wherein said outer sheath further comprises an inflow end portion extending beyond said inflow end of heart valve to define an implantation flange.

16. The heart valve prosthesis of claim 14 further comprising a substantially flexible annular ring positioned around said outer surface of said side wall portion spaced from and intermediate said outflow end of said heart valve, said outer sheath covering said ring and said heart valve.

17. The heart valve prosthesis of claim 16 further comprising sutures to maintain said ring positioned intermediate said inflow and outflow ends of said heart valve.

18. The heart valve prosthesis of claim 17 wherein said sutures secure said ring to said outer sheath.

19. The heart valve prosthesis of claim 17 wherein said sutures secure said ring to said side wall portion of said heart valve.

20. The heart valve prosthesis of claim 16 wherein said ring has a sinusoidal outflow edge corresponding to the contour of said outflow end of said heart valve.

21. The heart valve prosthesis of claim 16 further comprising a second sheath of natural tissue covering said side wall portion of said heart valve intermediate said ring and said heart valve, said second sheath extending between said inflow and outflow ends of said heart valve.

22. The heart valve prosthesis of claim 14 wherein each of said lobes extends a predetermined distance beyond and lateral to each of said commissures at said outflow end of said heart valve.

23. The heart valve prosthesis of claim 22 wherein each of said lobes comprises an ear-shaped flange.

24. The heart valve prosthesis of claim 14 wherein said heart valve comprises a composite heart valve formed of three heart valve leaflets of generally similar size, shape and symmetry, each said leaflet including a valve wall portion having an inflow end, an outflow end and a pair of generally opposed side edges extending between the inflow and outflow ends, said side edges of each of said leaflets being attached to said side edges of adjacent leaflets such that there is substantial coaptation between said leaflets, adjacent side edges of adjacent leaflets and associated valve wall portions defining said commissures, and said valve wall portions of said leaflets defining said side wall portion of said heart valve.

25. A method of making a heart valve prosthesis comprising the steps of:

provinding a natural tissue heart valve having an inflow end, an outflow end, a generally cylindrical side wall portion extending between said inflow end and said outflow end, said heart valve including a plurality of leaflets disposed within said side wall portion, each of said leaflets having a pair of side edges and an associated side wall portion, adjacent side edges of adjacent said leaflets and respective adjacent portions of said associated side wall portions defining commissures;

positioning an annular ring of a substantially flexible and resilient material around said side wall portion intermediate said inflow and outflow ends of said heart valve;

covering said annular ring and said outer surface of said heart valve with a sheath of natural tissue, an sheath having an inflow end portion and an outflow end portion; and extending said outflow end portion of said sheath beyond said outflow end of said heart valve to define a plurality of lobes adjacent said commissures.

26. The method of claim 25 further comprising the step of extending said inflow end portion of said sheath beyond said inflow end of said heart valve to form an annular implantation flange.

27. The method of claim 25 wherein said extending step further comprises extending each of said lobes a predetermined distance beyond and lateral to each of said commissures at said valve outflow end.

* * * * *